(12) United States Patent
Sabil

(10) Patent No.: US 12,066,361 B2
(45) Date of Patent: Aug. 20, 2024

(54) METHOD FOR ANALYZING SAMPLES OF A GAS IN A ROTARY CEMENT KILN

(71) Applicant: HOLCIM TECHNOLOGY LTD, Zug (CH)

(72) Inventor: Abderrahim Sabil, Holderbank (CH)

(73) Assignee: HOLCIM TECHNOLOGY LTD, Zug (CH)

( * ) Notice: Subject to any disclaimer, the term of this patent is extended or adjusted under 35 U.S.C. 154(b) by 475 days.

(21) Appl. No.: 17/294,092

(22) PCT Filed: Nov. 4, 2019

(86) PCT No.: PCT/IB2019/059431
§ 371 (c)(1),
(2) Date: May 14, 2021

(87) PCT Pub. No.: WO2020/099977
PCT Pub. Date: May 22, 2020

(65) Prior Publication Data
US 2022/0018739 A1   Jan. 20, 2022

(30) Foreign Application Priority Data

Nov. 15, 2018   (EP) ..................................... 18000901

(51) Int. Cl.
*G01N 1/22* (2006.01)
*G01N 33/00* (2006.01)
*G01N 33/38* (2006.01)

(52) U.S. Cl.
CPC ....... *G01N 1/2226* (2013.01); *G01N 33/0029* (2013.01); *G01N 33/0062* (2013.01); *G01N 33/383* (2013.01); *G01N 2001/2235* (2013.01)

(58) Field of Classification Search
CPC .................................................. G01N 1/2258
See application file for complete search history.

(56) References Cited

U.S. PATENT DOCUMENTS 4,059,019 A   11/1977   Wurster et al.
5,095,275 A * 3/1992   Dechene ................ G01N 27/60
                                                          324/454
(Continued)

FOREIGN PATENT DOCUMENTS

DE   25 35 646 A1   2/1977
DE   40 42 557 C2   11/1996
(Continued)

OTHER PUBLICATIONS

Machine translation of FR 232998 A1. Retrieved Sep. 28, 2023. (Year: 2023).*

(Continued)

*Primary Examiner* — Patrick Assouad
*Assistant Examiner* — Mark A Shabman
(74) *Attorney, Agent, or Firm* — Pillsbury Winthrop Shaw Pittman LLP

(57) ABSTRACT

In a method for analyzing samples of a gas in a rotary cement kiln by at least one gas sampling probe, a first and a second gas sampling probe are provided, wherein the first gas sampling probe is moved so as to reach a sampling position, wherein gas samples are withdrawn from the kiln and analyzed by the first gas sampling probe being in the sampling position, while the second gas sampling probe is kept in a retracted position and is purged, whereupon the second gas sampling probe is moved so as to reach a sampling position, and the first gas sampling probe is moved from the sampling position to the retracted position and is purged, while gas samples are withdrawn from the kiln and analyzed by the second gas sampling probe being in the sampling position.

7 Claims, 1 Drawing Sheet

(56) References Cited

U.S. PATENT DOCUMENTS

| | | | |
|---|---|---|---|
| 7,259,848 B2* | 8/2007 | Wittmer | G01J 3/0291 |
| | | | 356/319 |
| 2009/0000349 A1 | 1/2009 | Holt et al. | |
| 2010/0037678 A1* | 2/2010 | Chothani | G01N 27/14 |
| | | | 73/25.01 |
| 2011/0083745 A1* | 4/2011 | Saito | F27B 7/38 |
| | | | 137/897 |
| 2017/0038147 A1* | 2/2017 | Schürmann | C04B 7/364 |

FOREIGN PATENT DOCUMENTS

| | | |
|---|---|---|
| EP | 0324331 A1 | 7/1989 |
| EP | 0909942 B1 | 9/2002 |
| EP | 1 371 976 A1 | 12/2003 |
| FR | 2323998 A1 * 4/1977 | ........... G01N 1/2258 |

OTHER PUBLICATIONS

International Search Report as issued in International Patent Application No. PCT/IB2019/059431, dated Jan. 29, 2020.
Decision of Rejection as issued in Chinese Patent Application No. 201980075099.2, dated Apr. 29, 2024.

* cited by examiner

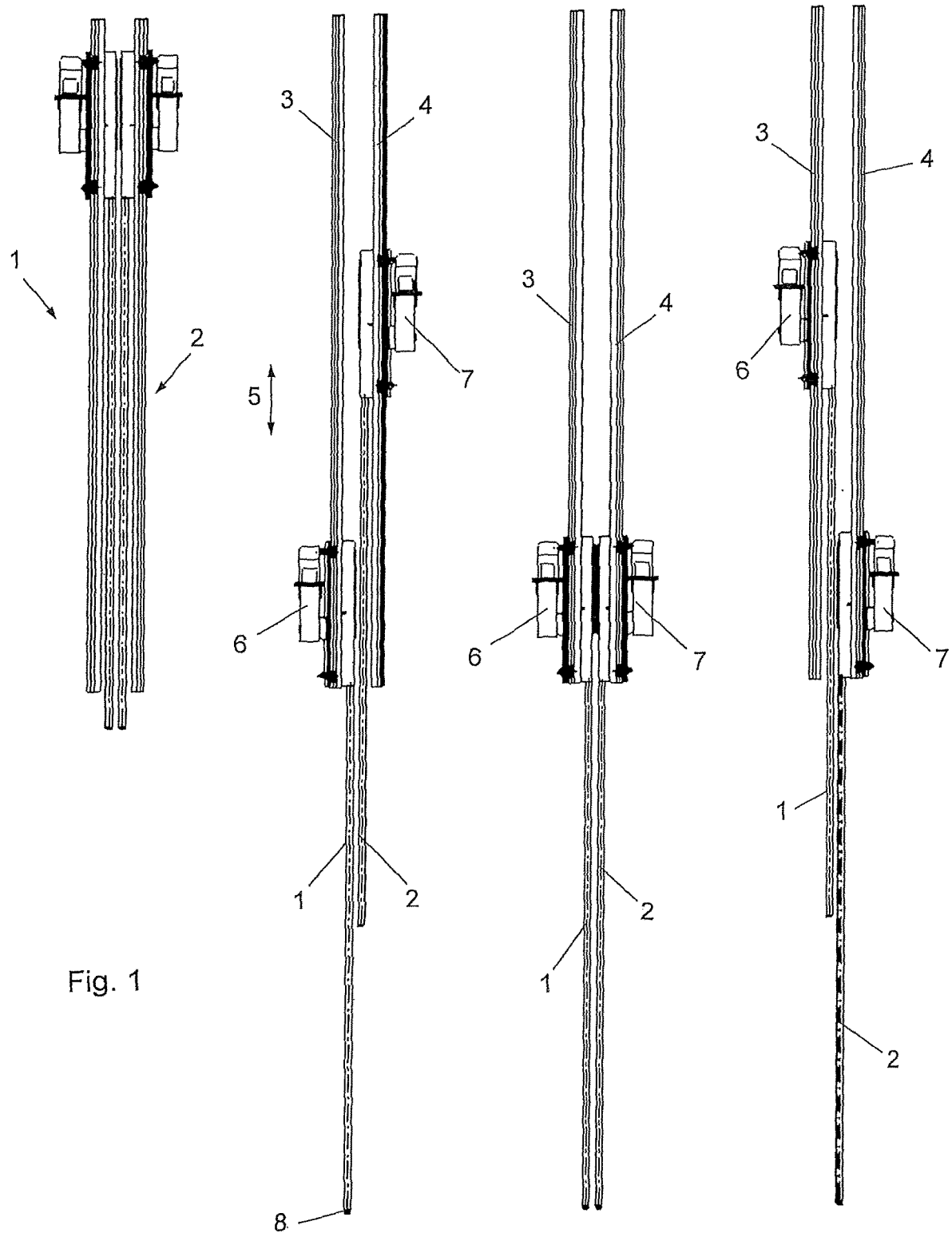

METHOD FOR ANALYZING SAMPLES OF A GAS IN A ROTARY CEMENT KILN

CROSS-REFERENCE TO RELATED APPLICATIONS

This application is the U.S. National Stage of International Application Serial No. PCT/IB2019/059431, filed Nov. 4, 2019, which in turn claims priority to European Application No. 18 000 901.1, filed Nov. 15, 2018. The contents of all of these applications are incorporated herein by reference in their entirety.

The invention refers to a method for analyzing samples of a gas in a rotary cement kiln by means of at least one gas sampling probe.

Further, the invention refers to a sampling device for carrying out the inventive method.

In known processes for producing cement clinker, raw material fed into a rotary kiln is preheated and partially decarbonated in a multistage preheater system by using the heat of combustion gases exhausted from the rotary kiln. The preheated raw material is fed into the rotary kiln via the kiln inlet and travels to the kiln outlet while being calcined at temperatures of up to 1400° C.

In order to control and optimize the kiln operation, it is a common procedure to analyze the process gases that are present in the rotary kiln in the region of the kiln inlet. The process gases are analyzed by using a gas sampling probe that is positioned to withdraw gas samples from the kiln inlet and to analyze the gas composition. The content of oxygen in the kiln is analyzed in order to control the risk of explosion and to prevent a toxic buildup of carbon monoxide. The measurement of the oxygen content also allows to control the air supply so as to change the burning rate to the desired level. Analyzing the process gases allows to control the burning process with the aim of minimizing emissions. Further, clinker quality can be controlled on basis of a process gas analysis. Finally, the content and the type of volatiles can be identified in order to prevent the occurrence of material built-ups and blockages and in order to reduce corrosion problems.

Known gas sampling probes comprise a tubular housing, into which the gas to be analyzed is constantly sucked through the tip of the probe. The gas is passed through a filter unit and is transported via a heated line into a heated sample chamber of the sampling analyzer. The gas analyzer is typically designed to measure the oxygen content (O2) and the amount of carbon monoxide (CO), nitrogen oxide (NO) and sulfur dioxide ($SO_2$) and in specific case methane ($CH_4$) and carbon dioxide ($CO_2$). The sensors located in the analyzer may be positioned so that the prevailing gas concentrations can accurately be determined in real time.

However, the conditions prevailing at the kiln inlet, such as in the kiln inlet chamber, in particular process temperatures of up to 1400° C., dust concentrations of up to 2000 g/m$^3$ and high mechanical stress make extreme demands on the equipment used for analyzing the process gas.

Therefore, the sampling procedure has to be interrupted at regular intervals for maintenance purposes. In particular, the sampling probe has to be retracted from the kiln and be cleaned. Usually, the sampling probe cannot be kept within the hostile environment of the kiln for longer than 30-60 minutes. During maintenance, the sampling procedure is interrupted so that a continuous gas analysis is not possible.

Therefore, the instant invention aims at improving a gas sampling method and a gas sampling device so as to allow for a continuous gas analysis over a long period of time, such as over several days, without any interruption.

In order to solve this object, the invention, in accordance with a first aspect thereof, provides a gas sampling method characterized essentially in that a first and a second gas sampling probe are provided, wherein the first gas sampling probe is moved so as to reach a sampling position, wherein gas samples are withdrawn from the kiln and analyzed by means of the first gas sampling probe being in the sampling position, while the second gas sampling probe is kept in a retracted position and is purged, whereupon the second gas sampling probe is moved so as to reach a sampling position, and the first gas sampling probe is moved from the sampling position to the retracted position and is purged, while gas samples are withdrawn from the kiln and analyzed by means of the second gas sampling probe being in the sampling position.

By providing two gas sampling probes instead of a single probe, one gas sampling probe can be used to withdraw gas samples, while the other gas sampling probe is retracted for maintenance, in particular for purging purposes. The two gas sampling probes are thus used alternatively for obtaining and analyzing gas samples. In this way, a continuous sampling process can be achieved.

Because the inventive method, by definition, allows for a continuous gas sampling, there is no need to maximize the residence time of a gas sampling probe within the kiln. This is in contrast to prior art methods, which aimed at maximizing the residence time within the kiln, in order to minimize the interruption time caused by the sampling probe undergoing maintenance outside of the kiln. Therefore, with the inventive method, the residence time of the first and the second gas sampling probe, respectively, can be chosen to be considerably shorter so as to prevent an excessive dust agglomeration on and within the gas sampling probe. In particular, the residence time of the first and the second gas sampling probe, respectively, within the kiln can be chosen to be 1-10 min, preferably 2-6 min, thereby preventing clogging of the probe.

In order to achieve an alternating operation of the first and the second gas sampling probe, a preferred embodiment of the invention provides that after the first gas sampling probe has been purged, the first gas sampling probe is moved so as to reach a sampling position, and the second gas sampling probe is moved from the sampling position to the retracted position and is purged, while gas samples are withdrawn from the kiln and analyzed by means of the first gas sampling probe being in the sampling position.

The inventive method is of particular interest for analyzing the process gas at the inlet of a rotary cement kiln. Therefore, a preferred embodiment provides that the first and the second gas sampling probe, respectively, is moved so as to reach a sampling position located at the kiln inlet or in the kiln inlet chamber, thereby allowing to withdraw gas samples from the kiln inlet or the kiln inlet chamber.

As known per se, the first and/or second gas sampling probe comprise a tubular housing, into which the gas to be analyzed can be sucked through the tip of the probe, wherein a filter is arranged within the tubular housing or at the extremity of the tubular housing and wherein the transfer line, downstream of the filter, is connected to a sample chamber comprising at least one gas analyzing sensor with a sampling system. Preferably, the gas analyzing sensor(s) is/are designed to measure the content or amount of oxygen ($O_2$), carbon monoxide (CO), methane ($CH_4$), nitrogen oxide (NO) and/or sulfur dioxide ($SO_2$).

According to a preferred embodiment, the first and the second gas sampling probes are guided for movement in a longitudinal direction between the retracted position and the sampling position. Preferably said longitudinal direction extends in the direction of the longitudinal axis of the tubular housing.

Preferably, the first and the second gas sampling probes are each driven in a longitudinal direction by means of a drive, such as a pneumatic drive or an electric drive.

Preferably, the first and the second gas sampling probes are arranged parallel and adjacent to each other, with their longitudinal axes being parallel to each other.

Purging of the gas sampling probes when in the retracted position can be performed in various ways. In their retracted position, the gas sampling probes are preferably located inside the kiln, but protected by a protective tube that surrounds the sampling tube. Preferably, the first and second gas sampling probes are each purged by means of a jet of compressed air preferably being blown through the sampling tube.

According to a second aspect, the invention provides a sampling device that may be used for carrying out a method according to the first aspect of the invention. The sampling device comprises a first and a second gas sampling probe that are each guided for movement between a retracted position and a sampling position by means of a respective drive. The gas sampling device further comprises a control unit that is connected with the drives of the first and second gas sampling probes for controlling movement between the retracted position and the sampling position and for starting and stopping gas analysis, wherein the control unit is configured to control the first and the second gas sampling probes so that the first gas sampling probe is moved so as to reach a sampling position, wherein gas samples are withdrawn from the kiln and analyzed by means of the first gas sampling probe being in the sampling position, while the second gas sampling probe is kept in a retracted position outside the kiln and is purged, whereupon the second gas sampling probe is moved so as to reach a sampling position, and the first gas sampling probe is moved from the sampling position to the retracted position and is purged, while gas samples are withdrawn from the kiln and analyzed by means of the second gas sampling probe being in the sampling position.

Preferably, the control unit is configured to control the first and the second gas sampling probes so that after the first gas sampling probe has been purged, the first gas sampling probe is moved so as to reach a sampling position, and the second gas sampling probe is moved from the sampling position to the retracted position and is purged, while gas samples are withdrawn from the kiln and analyzed by means of the first gas sampling probe being in the sampling position.

Preferably, the first and the second gas sampling probes are guided for movement in a longitudinal direction between the retracted position and the sampling position.

Preferably, the first and the second gas sampling probes are each driven in a longitudinal direction by means of a pneumatic drive or an electric drive.

Preferably, the first and second gas sampling probes each comprise a sampling tube for withdrawing a gas sample from the cement kiln through said sampling tube.

Preferably, purging means are provided for purging the first and second gas sampling probes when in their retracted position, said purging means preferably comprising blowing means for ejecting a jet of compressed air.

In the following, the invention will be explained in more detail by reference to the attached drawing. FIG. 1-4 show two gas sampling probes 1 and 2 in different positions during a cycle.

In FIG. 1 the first and the second gas sampling probes 1 and 2 are in their maintenance positions, in which they are located outside the rotary cement kiln. The first and the second gas sampling probes 1 and 2 are each guided on a guiding rail 3 and 4 for movement in the direction of the arrow 5. The movement is driven by pneumatic drives 6 and 7.

In FIG. 2, the first gas sampling probe 1 has been moved into the sampling position, wherein at least the probe tip 8 is located within the rotary cement kiln, in particular at the kiln inlet. The second gas sampling probe 2 is positioned in retracted position, in which it is purged by a purging device (not shown).

In FIG. 3 the second gas sampling probe 2 has also been moved into the sampling position.

In FIG. 4, the first gas sampling probe 1 has been retracted into the retracted position for cleaning purposes.

A continuous gas analysis is obtained by operating the gas sampling probes according to the following cycle:
a) First, probe 1 is in the sampling position and sampling gas, while probe 2 is in the retracted position for being purged (FIG. 2).
b) Then, probe 2 is moved to the sampling position, while probe 1 is still sampling gas (FIG. 3).
c) Then, probe 2 is starting sampling and probe 1 is moved to the retracted position for being purged (FIG. 4).
d) Then, probe 1 is moved to the sampling position, while probe 2 is still sampling gas (FIG. 3).
e) Then, probe 1 is starting sampling and probe 2 is moved to the retracted position for being purged (FIG. 2). This corresponds to step a) above.

Steps a) and c) may each last for approx. 3 minutes. Steps b) and d) may each last for approx. 1 minute.

Repeating said cycle results in a continuous gas sampling operation over a long period of time.

The invention claimed is:

1. A sampling device for analyzing samples of a gas in a rotary cement kiln by means of gas sampling probes, the sampling device comprising:
first and the second gas sampling probes that are each guided for movement between a retracted position and a sampling position by a respective drive, and
further comprising a control unit that is connected with the drives of the first and second gas sampling probes for controlling movement between the retracted position and the sampling position and for starting and stopping gas analysis, wherein the control unit is configured to control the first and the second gas sampling probes so that the first gas sampling probe is moved so as to reach the sampling position, wherein gas samples are withdrawn from the rotary cement kiln and analyzed by the first gas sampling probe being in the sampling position, while the second gas sampling probe is kept in the retracted position and is purged, whereupon the second gas sampling probe is moved so as to reach the sampling position, and the first gas sampling probe is moved from the sampling position to the retracted position and is purged, while gas samples are withdrawn from the kiln and analyzed by the second gas sampling probe being in the sampling position.

2. The sampling device according to claim 1, wherein the control unit is configured to control the first and the second gas sampling probes so that after the first gas sampling probe has been purged, the first gas sampling probe is moved so as to reach the sampling position, and the second gas sampling probe is moved from the sampling position to the retracted position and is purged, while gas samples are withdrawn from the kiln and analyzed by means of the first gas sampling probe being in the sampling position.

3. The sampling device according to claim 1, wherein the first and the second gas sampling probes are guided for movement in a longitudinal direction between the retracted position and the sampling position.

4. The sampling device according to claim 3, wherein the first and the second gas sampling probes are each driven in a longitudinal direction by a pneumatic drive or an electric drive.

5. The sampling device according to claim 1, wherein the first and second gas sampling probes each comprise a sampling tube for withdrawing a gas sample from the cement kiln through said sampling tube.

6. The sampling device according to claim 1, wherein a purge system is provided for purging the first and second gas sampling probes when in their retracted position.

7. The sampling device according to claim 6, wherein the purge system comprises a blowing system for ejecting a jet of compressed air.

* * * * *